US00PP29308P2

(12) United States Plant Patent
Kerley

(10) Patent No.: US PP29,308 P2
(45) Date of Patent: May 22, 2018

(54) ***BEGONIA* PLANT NAMED 'KERBESPICIT'**

(50) Latin Name: *Begonia tuberhybrida*
Varietal Denomination: KERBESPICIT

(71) Applicant: Timothy Kerley, Over (GB)

(72) Inventor: Timothy Kerley, Over (GB)

( * ) Notice: Subject to any disclaimer, the term of this patent is extended or adjusted under 35 U.S.C. 154(b) by 0 days. days.

(21) Appl. No.: 15/530,705

(22) Filed: Feb. 17, 2017

(51) Int. Cl.
*A01H 5/02* (2018.01)

(52) U.S. Cl.
USPC ..... Plt./344

(58) Field of Classification Search
USPC ..... Plt./344
See application file for complete search history.

*Primary Examiner* — Annette H Para
(74) *Attorney, Agent, or Firm* — Cassandra Bright

(57) ABSTRACT

A new and distinct *Begonia tuberhybrida* cultivar named 'KERBESPICIT' is disclosed, characterized by cream yellow colored, strongly fragrant flowers. Plants are mounded to semi-upright, free-branching with excellent weather tolerance. The new variety is a *Begonia*, and is normally used as an ornamental garden or container plant.

2 Drawing Sheets

Latin name of the genus and species: *Begonia tuberhybrida.*

Variety denomination: 'KERBESPICIT'.

BACKGROUND OF THE INVENTION

The new cultivar is the product of a planned breeding program. The new variety originated as the result of a crossing performed during September of 2009 of *Begonia* 'Fragrant Blush'(unpatented) with the pollen parent, *Begonia tuberhybrida* 'Helene Harms'(unpatented). The selection of the new variety was made in July 2010, by the inventor at a research greenhouse located in Cambridge, UK.

Asexual reproduction of the new cultivar 'KERBESPICIT' was first performed at a research greenhouse located in Cambridge, UK by terminal vegetative cuttings during February 2011. 'KERBESPICIT' has since produced several generations by vegetative cuttings and has shown that the unique features of this cultivar are stable and reproduced true to type.

SUMMARY OF THE INVENTION

The cultivar 'KERBESPICIT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBESPICIT.' These characteristics in combination distinguish 'KERBESPICIT' as a new and distinct *Begonia tuberhybrida* cultivar:

1. Mounding to semi-trailing plant habit.
2. Strongly fragrant flowers.
3. Cream Yellow flower color, without pink blush.
4. Free branching.
5. Medium flower size.
6. Excellent weather tolerance
7. Suitability for pot sizes 12 cm and larger.
8. Flowers upwardly or outwardly facing.

PARENT COMPARISON

Plants of the new cultivar 'KERBESPICIT' are similar to plants of the seed parent variety in most horticultural characteristics. However, plants of the new cultivar 'KERBESPICIT' differ in the following:

1. Flowers of the new variety are cream yellow, flowers of the seed parent are cream with pink blush.
2. Plants of the new variety have a mounding to semi-trailing habit, plants of the seed parent are more upright.
3. Stems of the new variety are smaller in diameter than the seed parent.
4. Plants of the new variety branch more abundantly than the seed parent.

Plants of the new cultivar 'KERBESPICIT' are similar to plants of the pollen parent variety in most horticultural characteristics. However, plants of the new cultivar 'KERBESPICIT' differ in the following:

1. Flowers of the new variety are larger than flowers of the pollen parent.
2. Flowers of the new variety are strongly fragrant, flowers of the pollen parent are unscented.
3. Flower color of the new variety is a much lighter yellow.

COMMERCIAL COMPARISON

Plants of the new cultivar 'KERBESPICIT' are similar to plants of the commercial variety, *Begonia* 'Fragrant Falls Lemon Fizz', in most horticultural characteristics. However, plants of the new cultivar 'KERBESPICIT' differ in the following:

1. Flowers of the new variety are a lighter yellow color.
2. Flowers of the new variety are smaller than those of this comparator.
3. Plants of the new variety are more free branching than this comparator.
4. Plants of the new variety are mounding to semi-upright, plants of this comparator are upright, then lodging over with age.

Plants of the new cultivar 'KERBESPICIT' are similar to plants of the commercial variety, *Begonia* '77KL Sunrise', U.S. Plant Pat. No. 12,808, in most horticultural characteristics. However, plants of the new cultivar 'KERBESPICIT' differ in the following:

1. Flowers of the new variety are a lighter yellow color.
2. Flowers of the new variety are smaller than those of this comparator.
3. Plants of the new variety are more free branching than this comparator.
4. Plants of the new variety are mounding to semi-upright, plants of this comparator are upright, then lodging over with age.
5. Flowers of the new variety are upwardly or outwardly facing, flowers of the comparator are pendulous and downward facing.

BRIEF DESCRIPTION OF THE PHOTOGRAPH

The present invention of a new and distinct variety of *Calendula* is shown in the accompanying photographs, the colors being as nearly true as possible with color photographs of this type.

DETAILED BOTANICAL DESCRIPTION

Figure 1:
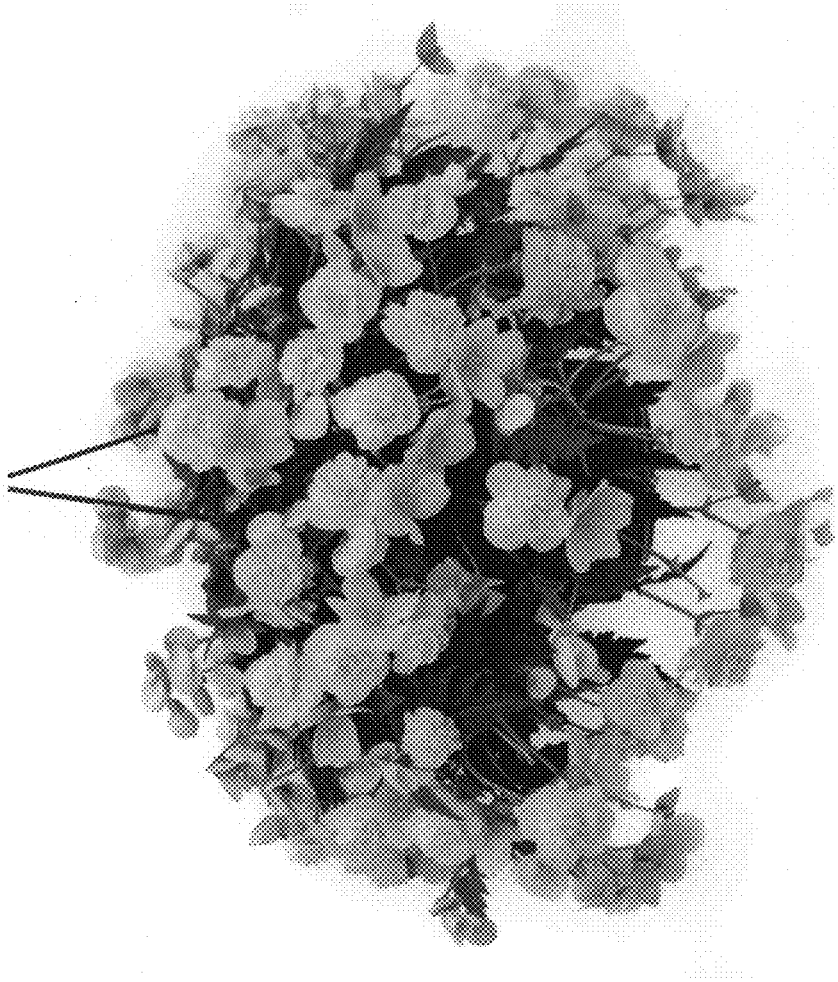
FIG. 1 illustrates a plant of approximately 5 months in a 20 cm pot
Figure 2:
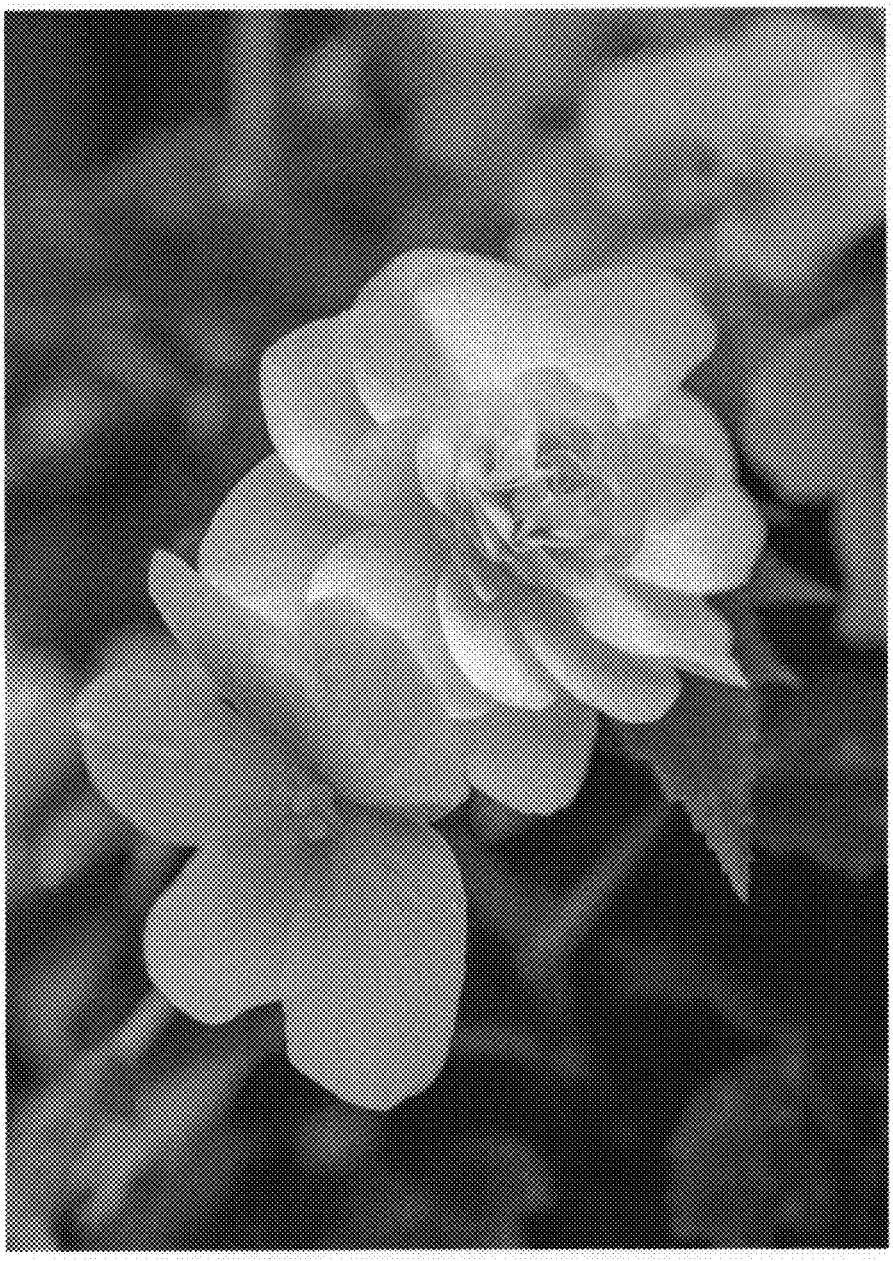
FIG. 2 illustrates a close up of the inflorescence.

In the following description, color references are made to The Royal Horticultural Society Colour Chart 2001 except where general terms of ordinary dictionary significance are used. The following observations and measurements describe 'KERBESPICIT' plants grown in a commercial controlled greenhouse in Cambridge, United Kingdom. Measurements and numerical values represent averages of typical plant types.

Botanical classification: *Begonia tuberhybrida* 'KERBESPICIT'.

Age of plant described: Approximately 15 weeks.

Container of plant described: Hanging basket.

PROPAGATION

Type of propagation typically used: Vegetative tip cuttings.

Time to develop roots: About 10 days at approximately 21° C.

Time to develop a rooted liner: About 21 days at approximately 21° C.

Root description: Fibrous, fine, well branched. White and tan, not accurately measured with the R.H.S. chart.

PLANT

Growth habit: Mounding to semi-upright.

Height: 15 cm.

Plant spread: 29 cm.

Growth rate: Moderate.

Branching characteristics: Well branched.

Characteristics of primary lateral branches:

- *Form*.—Round in cross section.
- *Length*.—Approximately 17 cm.
- *Diameter*.—Approximately 0.9 cm.
- *Color*.—Near RHS Yellow-Green with a hint of Greyed-Orange 174B.
- *Texture*.—Mainly glabrous, infrequent pubescence.
- *Strength*.—Moderately strong and flexible.

Internode length: Average 3.2 cm.

FOLIAGE

Arrangement: Alternate.

Quantity: Approximately 8 per primary lateral branch.

Average length: Approximately 12.0 cm.

Average width: Approximately 6.0 cm.

Shape of blade: Cordate.

Apex: Acute.

Base: Cordate.

Margin: Double serrate.

Texture of top surface: Slightly pubescent, hairs approximately 2 mm.

Texture of bottom surface: Slightly pubescent, hairs approximately 2 mm.

Aspect: Strong upward curve to overall leaf, margins slightly curled under.

Color:

- *Young foliage upper side*.—Darker than Yellow-Green 148A.
- *Young foliage under side*.—Near RHS Yellow-Green 147C.
- *Mature foliage upper side*.—Near RHS Yellow-Green 147A.
- *Mature foliage under side*.—Near RHS Yellow-Green 147B.

Venation:

- *Type*.—Palmate.
- *Venation color upper side*.—Near RHS Yellow-Green 146C.
- *Venation color under side*.—Between RHS Yellow-Green 147C.

Petiole:

- *Length*.—Approximately 4 cm.
- *Diameter*.—Approximately 0.4 cm.
- *Color*.—Near RHS Greyed-Orange 174A.
- *Texture*.—Pubescent.

Stipule description: Usually 1 per leaf, occasionally 2.

- *Length*.—Approximately 0.6 cm.
- *Diameter*.—Approximately 0.5 cm.
- *Color*.—Near RHS Yellow-Green 146D.
- *Texture*.—Glabrous.

FLOWER

Flowering season: May to September in Cambridge, UK.

Flower type and habit: Double male flowers, single female flowers, arranged either as 1 male and 1 female, or 1 male the 2 female flowers.

Quantity: About 28 per plant.

Persistent or self-cleaning: Self-Cleaning.

Bud:

- *Shape*.—Orbicular.
- *Length*.—Approximately 1.8 cm.
- *Diameter*.—Approximately 1.6 cm.
- *Color*.—Near Yellow 11D, flushed Red 37B.

Flower size:

- *Male*.—Diameter: Approximately 6.0 cm. Depth: Approximately 2.0 cm.
- *Female*.—Diameter: Approximately 6.0 cm. Depth: Approximately 0.75 cm.

Tepals:

*Quantity*.—Male: Approximately 55 to 63. Female: 5.

*Arrangement*.—Rosette.

*Length*.—Longest, approximately 3.5 cm.

*Width*.—Approximately 3.6 cm.

*Shape*.—Obovate.

*Apex*.—Obtuse.

*Base*.—Rounded.

*Margin*.—Entire.

*Texture, upper and lower surfaces*.—Matte.

*Color*.—Male Outer Tepals When opening, upper surface: Near Yellow 10D, margin Orange-White 159C. Base Yellow 10B. When opening, lower surface: Near Orange-White 159C, margin 159C, base 10A. Male Inner Tepals When opening, upper surface: Near Yellow 10D, base 10A. When opening, lower surface: Near Yellow 10C, margin 10D. Male Outer Tepals Fully opened, upper surface: Near Yellow 9A, margin White 155D. Base Yellow-Orange 17A. Fully opened, lower surface: Near White 155A, transitioning to Yellow-Orange 23B at base. Male Inner Tepals Fully opened, upper surface: Near Yellow 9C, margin 155D. Base 9A. Fully opened, lower surface: Near 155A, base 155C.

*Color*.—Female Flower Tepals Immature, upper surface: Near 5A, fading to 5D towards margin. Margin 4D. Immature, lower surface: Near Yellow 5D, fading to 4d towards margin. Fully opened, upper surface: Near Yellow-Orange 23A near base, transitioning to Yellow 9A towards margin. Margin 4D. Fully opened, lower surface: Near Yellow-Orange 23B near base, transitioning to 159B towards margin.

Flower bracts:

*Quantity per flower*.—2, opposite.

*Shape*.—Ovate.

*Length*.—Approximately 1.1 cm.

*Diameter*.—Approximately 0.6 cm.

*Apex*.—Obtuse.

*Margin*.—Entire.

*Texture*.—Glabrous.

*Color*.—Near RHS Yellow-Green 152D, flushed Greyed-Red 178C.

Peduncles:

*Length*.—Average 5.9 cm.

*Diameter*.—Approximately 0.5 cm.

*Angle*.—About 15° to the lateral branch.

*Strength*.—Moderate, flexible.

*Texture*.—Glabrous, shiny.

*Color*.—Near Yellow-Green 145B, flushed Greyed-Red 178A on mature flowers. Immature flowers 145B with no flush.

Pedicels:

*Length*.—Approximately 2.8 cm.

*Diameter*.—Approximately 0.3 cm.

*Angle*.—About 15° to the lateral branch.

*Strength*.—Moderate, flexible.

*Texture*.—Glabrous, shiny.

*Color*.—Mature flowers ear Yellow-Green 145A, flushed Greyed-Red 178C. Immature flowers Yellow-Green 144B.

Fragrance: Strongly scented.

REPRODUCTIVE ORGANS

Androecium: Not observed.

Pistil: Highly reduced, minute multi-lobed stigma present.

OTHER CHARACTERISTICS

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

Other features: Excellent weather tolerance.

What is claimed is:

1. A new and distinct cultivar of *Begonia* plant named 'KERBESPICIT' as herein illustrated and described.

* * * * *